United States Patent [19]
Oshima et al.

[11] Patent Number: 5,242,818
[45] Date of Patent: Sep. 7, 1993

[54] **METHOD OF PRODUCING A THERMOSTABLE DNA POLYMERASE FROM *THERMUS THERMOPHILUS***

[75] Inventors: Tairo Oshima, Machida; Hitoshi Sakashita; Hakuji Matsumoto, both of Ohtsu; Yoshihiko Maekawa, Tsuruga, all of Japan

[73] Assignee: Toyo Boseki Kabushiki Kaisha, Osaka, Japan

[21] Appl. No.: 893,735

[22] Filed: Jun. 5, 1992

Related U.S. Application Data

[62] Division of Ser. No. 398,178, Aug. 24, 1989.

[30] Foreign Application Priority Data

Aug. 26, 1988 [JP] Japan .................. 63-213330

[51] Int. Cl.$^5$ .................................... C12N 11/12
[52] U.S. Cl. .......................................... 435/194
[58] Field of Search ................................. 435/194

[56] References Cited

U.S. PATENT DOCUMENTS 4,889,818  12/1989  Gelfand et al. .............. 435/194

FOREIGN PATENT DOCUMENTS 0258017  3/1988  European Pat. Off. .

OTHER PUBLICATIONS

R. K. Saiki et al., "Enzymatic Amplification of β--Globin Genomic Sequences and Restriction Site Analysis for Diagnosis of Sickle Cell Anemia," *Science*, 230, 1350–1354 (1985).

R. K. Saiki et al., "A Novel Method for the Detection of Polymorphic Restriction Sites by Cleavage of Oilgonucleotide Probes: Application to Sickle-Cell Anemia," *Bio/Technology*, 3, 1008–1012 (1985).

C. Ruttiman et al., "DNA polymerases from the extremely thermophilic bacterium *Thermus thermophilus* HB-8," *European Journal of Biochemistry*, 149, 41–46 (1985).

A. Chien et al., "Deoxyribonucleic Acid Polymerase from the Extreme Thermophile *Thermus aquaticus*," Journal of Bateriology, vol. 127 No. 3, pp. 1550–1557 (Sep. 1976).

Stoesz et al. (1978) *Biochemistry*, 17(18), 3693–3699.
Hon-Nami et al. (1979) *Biochemistry*, 18(25), 5693–5697.
Elie et al. (1989) *Eur. J. Biochem.*, 178(3), 619–626.
Bechtereva et al. (1989) *Nucleic Acids Res.*, 17(24), 10507.
Innis et al. (1990) *Pcr. Protocol: Guide Methods Appl.*, pp. 129–141, Acad. Press, San Diego, Calif.

*Primary Examiner*—Douglas W. Robinson
*Assistant Examiner*—Jon P. Weber
*Attorney, Agent, or Firm*—Leydig, Voit & Mayer

[57] ABSTRACT

A DNA polymerase with excellent thermostability is provided. The DNA polymerase retains at least about 60% of its activity when placed at pH 8.0 for 2 hours at 85° C.

1 Claim, 3 Drawing Sheets

METHOD OF PRODUCING A THERMOSTABLE DNA POLYMERASE FROM *THERMUS THERMOPHILUS*

This is a divisional of copending application Ser. No. 07/398,178, filed on Aug. 24, 1989.

BACKGROUND OF THE INVENTION

1. Field of the Invention

The present invention relates to a thermostable DNA polymerase and a method for producing the same. More particularly, the present invention relates to an excellent thermostable DNA polymerase which is produced by microorganisms of the genus Thermus, for example, *Thermus thermophilus*, and a method for the production of this DNA polymerase.

The thermostable DNA polymerase of the present invention is an enzyme which catalyzes a synthesis of DNA complementary to a template DNA from the template DNA primer and four varieties of deoxyribonucleoside triphosphates. This enzyme is used in gene manipulation techniques such as the amplification of nucleic acid sequences and the determination of DNA base sequences.

2. Description of the Prior Art

Thermostable DNA polymerase derived from *Thermus aquaticus* YT-I (ATCC 25104) has been known previously. A. Chien et al. (J. Bacteriol. Vol. 127, pp. 1550-1557, 1976) reported a method for the isolation and purification of DNA polymerase from *Thermus aquaticus* YT-I, and also reported on the enzymatic properties (i.e., optimal temperature, optimal pH and effects of divalent ion concentrations, etc.) of this polymerase.

Nucleic acid sequences can be effectively amplified by using such thermostable DNA polymerases. A method of amplifying nucleic acid sequences using the above-mentioned thermostable DNA polymerase derived from *Thermus aquaticus* YT-I (hereinafter referred to as Taq polymerase) has been reported by Saiki et al. (Science, Vol 230, pp. 1350-1354, 1985; Bio/Technology, Vol. 3, pp. 1008-1012, 1985; and Japanese Laid-Open Patent Publication No. 63-102677). This method includes the following processes.

1) A double-stranded DNA sequence is denatured to prepare a single-stranded sequence.
2) The single-stranded template nucleotide chain so obtained is annealed with a primer.
3) The said primer is elongated.

In this procedure, heat is applied during process 1, while DNA polymerase acts in process 3. Since the said DNA polymerase is thermostable, deactivation hardly occur in returning to process 1 subsequent to process 3. That is, the successive processes 1 through 3 can be repeated continuously, and therefore the amplification of the nucleotide chain can be effectively performed. However, even if Taq polymerase is used when the processes 1 through 3 are continuously repeated, particularly in the denaturation process 1 where temperatures of about 90° to 105° C. are applied, enzymatic activity does diminish and therefore adequate amplification cannot be obtained.

Thus, an adequately thermostable DNA polymerase has not previously been obtained, and the development of a DNA polymerase of high thermostability is desirable.

SUMMARY OF THE INVENTION

The DNA polymerase with excellent thermostability of this invention, which overcomes the above-discussed and numerous other disadvantages and deficiencies of the prior art, retains at least about 60% of its activity when placed at pH 8.0 for 2 hours at 85° C.

In a preferred embodiment, the DNA polymerase is derived from microorganisms of the genus Thermus.

A method for producing the DNA polymerase of this invention comprises the steps of, culturing a microorganism of the genus Thermus in a culture medium, and recovering the produced thermostable DNA polymerase having above-mentioned characteristics.

In a preferred embodiment, the said DNA polymerase has the following characteristics: (1) It catalyzes the elongation reaction of nucleotide sequence that is complementary to the template nucleotide sequence, using nucleoside triphosphates as substrates; (2) Its optimal pH is approximately 8 0; (3) Its optimal temperature is approximately 75° C.; (4) It requires magnesium ions, and the optimal magnesium ion concentration being in the range from 6 to 20 mM; (5) Its optimal saline concentration is approximately 20 to 60 mM of sodium chloride or potassium chloride; and (6) Its molecular weight is approximately 85,000 to 95,000 daltons (measured by SDS polyacrylamide gel electrophoresis).

Thus, the invention described herein makes possible the objectives of (1) providing DNA polymerase with excellent thermostability; (2) providing a highly thermostable DNA polymerase which is advantageous for utilization in gene amplification; and (3) providing an effective method for the production of the aforesaid thermostable DNA polymerase.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
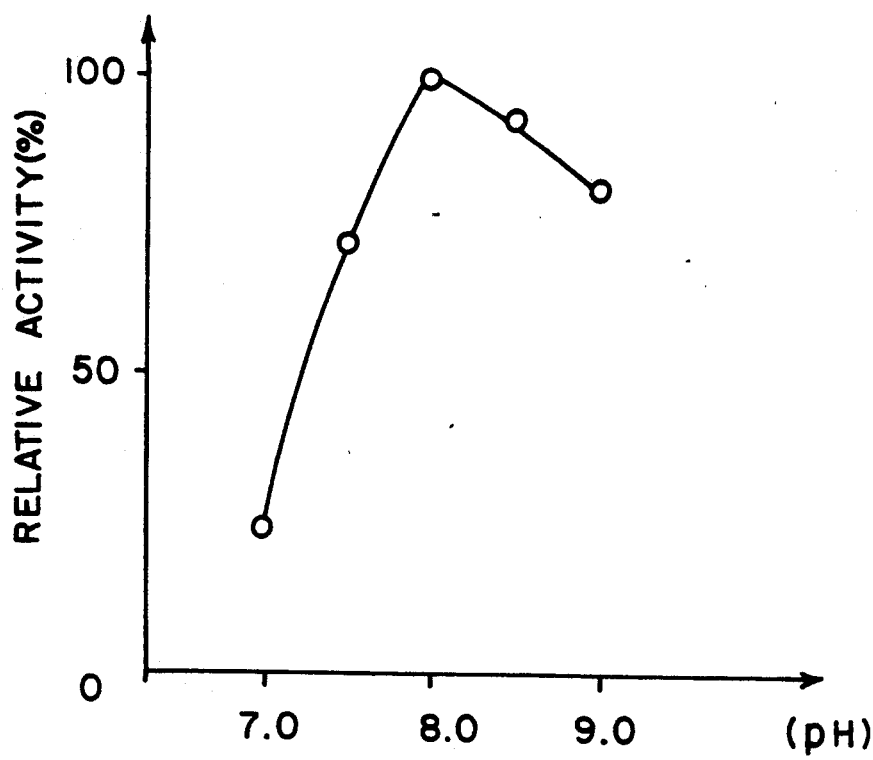
FIG. 1 shows the optimal pH for the thermostable DNA polymerase of the present invention.

The present inventors have conducted intensive research with the objective of finding a DNA polymerase with even greater thermostability than existing thermostable DNA polymerases, and have thereby succeeded in finding a thermostable DNA with superior thermostability, derived from bacterial strains of the genus Thermus.

As the bacterial strains producing the enzyme of the present invention, certain strains belonging to the genus Thermus, for example, *Thermus thermophilus* HB8 (ATCC 27634) can be listed.

In order to produce the enzyme of the present invention, first, a bacterial strain of the genus Thermus, e.g., *Thermus thermophilus* HB8 (ATCC 27634) is cultivated in the usual manner.

Either a synthetic or a natural culture medium can be used for this purpose, merely provided that the composition includes appropriate proportions of the carbon sources, nitrogen sources, inorganic substances and other necessary nutrients which can be assimilated by the bacterial strain being used. For example, glucose, sucrose, dextrin or molasses can be used as a carbon source, while either inorganic or organic nitrogen compounds can be used as nitrogen sources. These include, for example, natural nitrogenous substances such as peptones, meat extracts, yeast extracts and casein hydrolysates, inorganic salts such as ammonium chloride and ammonium sulphate, etc., and amino acids such as glutamic acid, etc.

Using the above-mentioned medium, the aforesaid bacteria can ordinarily be cultivated by shaking culture or by aerated spinner culture. The incubation temperature should be maintained in the range of 50° to 80° C., preferably at about 75° C., and the pH in the range of 5 to 10, preferably between pH 7 and 9. Cultivation under conditions other than these is also possible, merely provided that such conditions permit the growth of the bacterial strain being used. The incubation time is ordinarily from 1 to 3 days; during this period, the bacteria grow and DNA polymerase is produced and accumulated within the bacterial cell bodies.

The enzyme of the present invention is extracted from the bacterial cell bodies and purified by conventional methods. The methods of extraction which can be employed for this purpose include ultrasonic disintegration, mechanical fragmentation using glass beads, the French press method, or dissolution of the bacterial cell membranes using a surfactant, etc. The liquid extract (i.e., crude enzyme liquid) obtained in this manner can be purified by salting out with ammonium sulphate or sodium sulphate, etc., or by metallic condensation methods using magnesium chloride or calcium chloride, or by ion exchange chromatography using diethylaminoethyl (DEAE) Sepharose, carboxymethyl (CM) Sepharose, etc.

The activity of the DNA polymerase so obtained can be assayed as follows.

Composition of reagent for assay of enzymatic activity 500 mM Tris buffer, pH 8.0 (at 25° C.)
100 mM magnesium chloride
2 mM dATP, dCTP and dGTP
2 mM tritium-labelled TTP
100 mM 2-mercaptoethanol A 5 µl aliquot of 1 µg/µl activated calf thymus DNA and then 35 µl of distilled water are added to 5 µl of the reagent obtained by mixing the above ingredients. To 45 µl of this mixture is added 5 µl of the present enzyme, and after gentle mixing the mixture is incubated at 75° C. for 30 minutes. After the completion of this reaction, the mixture is placed on ice and after adding of 50 µl of 0.1 M sodium pyrophosphate and 100 µl of 1M perchloric acid is left standing on ice for at least 1 hour. Next, this mixture is filtered through a GF/C filter (Whatman Co.). This filter is then successively washed with 0.1N hydrochloric acid and cold ethanol, and the tritium content of the filter is then measured with a liquid scintillation counter (Aloka LSC-700). In this manner, the quantity of tritium-labelled TTP incorporated into the acid-insoluble fraction is calculated. The quantity of DNA polymerase such that 10 nmoles of TTP is incorporated into the acid-insoluble fraction under the above conditions during a 30 minute period is defined as 1 unit (U).

The physicochemical properties of the enzyme of the present invention are as follows.

Action and substrate specificity: it catalyzes the elongation reaction of nucleotide sequence that is complementary to the template nucleotide sequence, using nucleoside triphosphates as substrates.

Optimal pH: approximately 8.0
Optimal temperature: approximately 75° C.
Thermostability: it retains at least about 60% of its activity when placed at pH 8.0 for 2 hours at 85° C.
Required metallic ions: magnesium ions, the optimal concentration of which is between 6 and 20 mM.
Optimal salt concentration: 20 to 60 mM (sodium chloride or potassium chloride)
Molecular weight: approximately 85,000 to 95,000 daltons (measured by SDS-polyacrylamide gel electrophoresis).

EXAMPLE

The present invention is illustrated by the following example.

First, 100 ml of culture medium (pH 7.5) containing 1.0% polypeptones, 0.5% yeast extract and 0.2% sodium chloride was placed in a Sakaguchi flask and sterilized in an autoclave at 121° C. for 15 minutes. After being left to cool, the medium was inoculated with *Thermus thermophilus* HB8 (ATCC 27634), using a platinum loop. The mixture was aerobically cultured for 24 hours at 70° C., and used as the seed culture. Next, 6 liters of fresh medium of the same composition was placed in a 10 liters jar fermentor, which was then heated for 15 minutes at 121° C. in an autoclave and left to cool. Then, 100 ml of the above-mentioned seed culture fluid was transferred to this jar fermentor, and this was incubated at 70° C. for 10 hours at a rotary speed of 400 rpm and an aeration rate of 2 liters/min.

The bacteria cells were separated from 6 liters of this culture broth by centrifugation and resuspended in a potassium phosphate buffer containing 10 mM 2-mercaptoethanol and 5% glycerol, pH 7.5 (referred to as Buffer A). This suspension was treated for 20 minutes in a sonicator (19 kHz; Kaijo Electric Co.), then centrifuged, and the supernatant was collected. After dialysis, the obtained liquid was subjected to chromatography in a column packed with DEAE Sepharose CL-6B (Pharmacia) equilibrated with Buffer A, and was eluted from the column by means of a sodium chloride density gradient, also using Buffer A. DNA polymerase activity was found in the eluted fraction containing 0 to 0.5 M sodium chloride. This active fraction was dialyzed against Buffer A. The dialyzed fluid was then subjected to chromatography in a column packed with phosphocellulose P-11 (Whatman) equilibrated with Buffer A, and again sodium chloride gradient elution was performed using Buffer A. DNA polymerase activity was detected in the fraction containing 0–0.5M sodium chloride. The active fraction was dialyzed against Buffer A, and then this dialyzed fluid was subjected to column chromatography in a column packed with Native DNA cellulose (Pharmacia) equilibrated with Buffer A. Again, sodium chloride density gradient elution was performed, and 1,200 U of DNA polymerase was obtained from the eluate fraction containing 0–0.5M sodium chloride.

The physicochemical properties of the DNA polymerase so obtained were examined as follows.

(1) Optimal pH

The influence of reaction pH upon the aforesaid DNA polymerase was examined, using 50 mM tris(hydroxymethyl)aminomethane HCl buffer. The results of measuring activity at various pH values were as shown in FIG. 1. As can be seen from FIG. 1, the optimal pH is approximately 8.0.

(2) Optimal temperature

Figure 2:
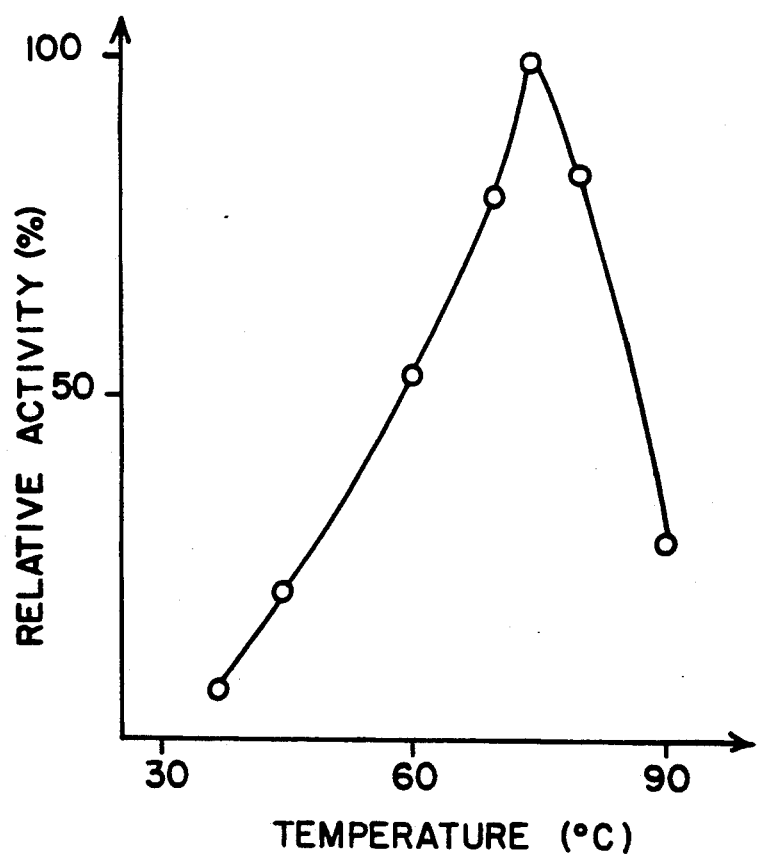
FIG. 2 shows the optimal temperature for the thermostable DNA polymerase of the present invention.

The results of measuring enzymatic activity at various temperatures were as shown in FIG. 2. As can be seen from FIG. 2, the optimal temperature is approximately 75° C.

(3) Optimal magnesium ion concentration

Figure 3:
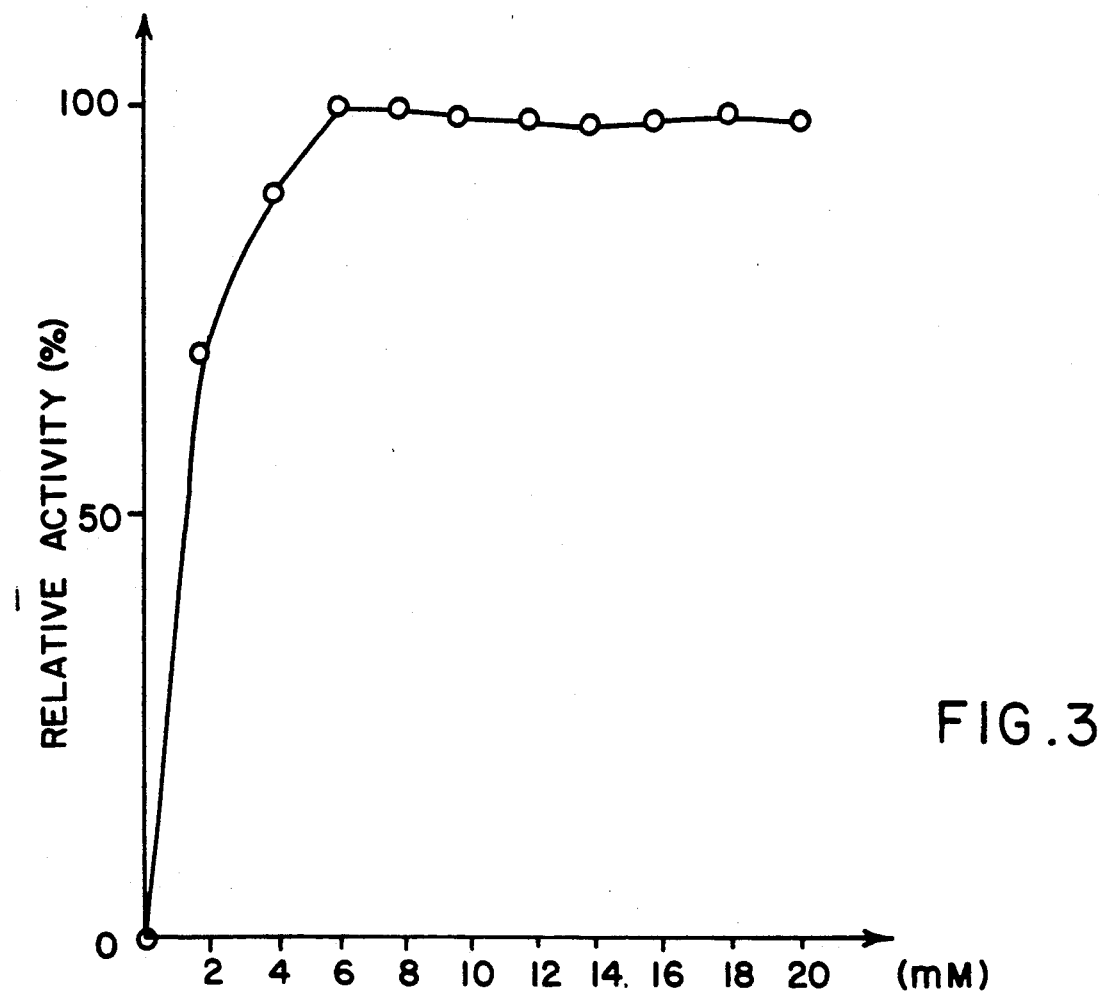
FIG. 3 shows the optimal magnesium ion concentration for the thermostable DNA polymerase of the present invention.

The magnesium ion concentration of the reagent used for measuring the activity of the present enzyme was varied, while the other conditions were maintained unchanged, and the results so obtained are shown in FIG. 3. As can be seen from FIG. 3, the optimal magnesium concentration is approximately 5 to 20 mM.

Figure 4:
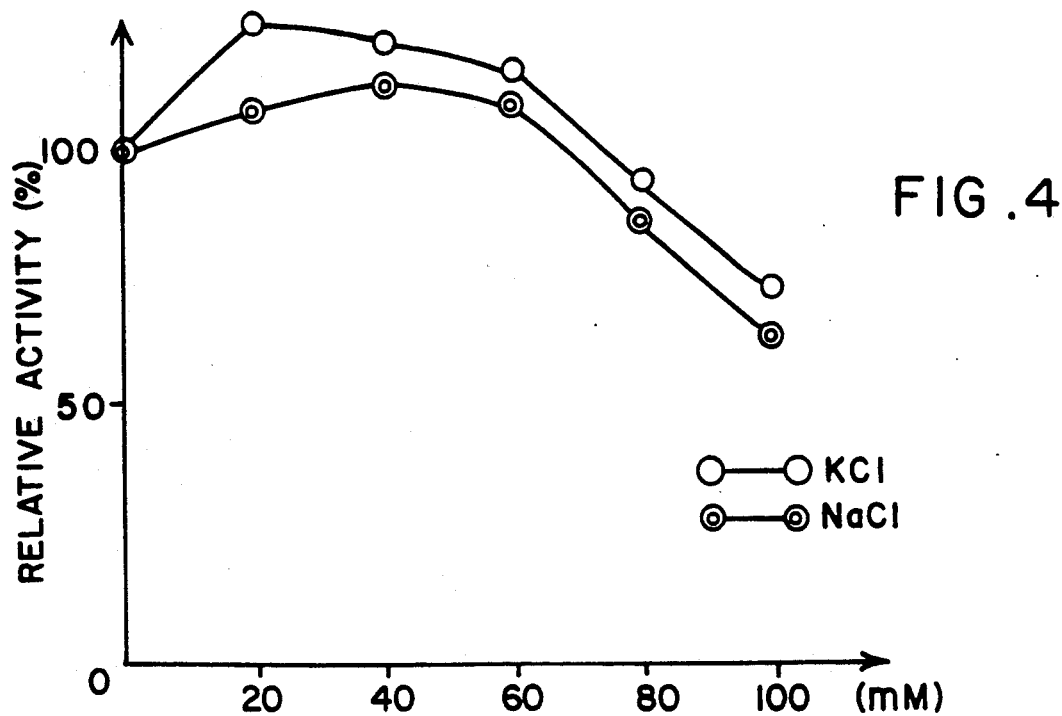
FIG. 4 shows the optimal salt concentration for the thermostable DNA polymerase of the present invention.

(4) Optimal salt concentration 50 mM Tris HCl buffer (pH 8.5)
10 mM magnesium chloride
10 mM 2-mercaptoethanol
200 μM dNTP (including tritium labelled dTTP)
5 μg activated calf thymus DNA
Sodium chloride or potassium chloride (quantities corresponding to concentrations shown in FIG. 4)

The above constituents were mixed to obtain a 50 μl mixture, and the prescribed quantities of the present enzyme were added to this mixture. After gentle blending, the mixture was allowed to react at 70° C. for 30 min. and the activity was measured. The results were as shown in FIG. 4. The single and double circles in this figure indicate values of relative activity measured using potassium chloride and sodium chloride, respectively.

(5) Thermostability 67 mM Tris HCl buffer (pH 8.8)
16.6 mM ammonium sulfate
6.7 mM magnesium chloride
10 mM 2-mercaptoethanol
170 μg/ml BSA First, 100 ml of a buffer solution containing the above constituents was prepared, and 2 U of the enzyme of the present invention was added to this buffer. The mixture was incubated for 2 hours, at a prescribed temperature ranging from 75° to 98° C., after which the residual enzymatic activity was assayed. As a control, the same experiment was performed with commercially marketed thermostable DNA polymerase (New England Biolabo) derived from *Thermus aquaticus* YT-I. The residual activities of the enzyme of this invention and the enzyme derived from *Thermus aquaticus* YT-I are shown Table 1.

TABLE 1

| | Enzyme derived from *Thermus thermophilus* | Enzyme derived from *Thermus aquaticus* |
|---|---|---|
| | Residual activity (%) | |
| 70° C. | 40.3 | 71.5 |
| 75° C. | 44.3 | 70.3 |
| 85° C. | 37.7 | 62.6 |
| 93° C. | 30.1 | 55.4 |
| 95° C. | 27.7 | 30.0 |
| 98° C. | 0 | 0 |

Figure 5:
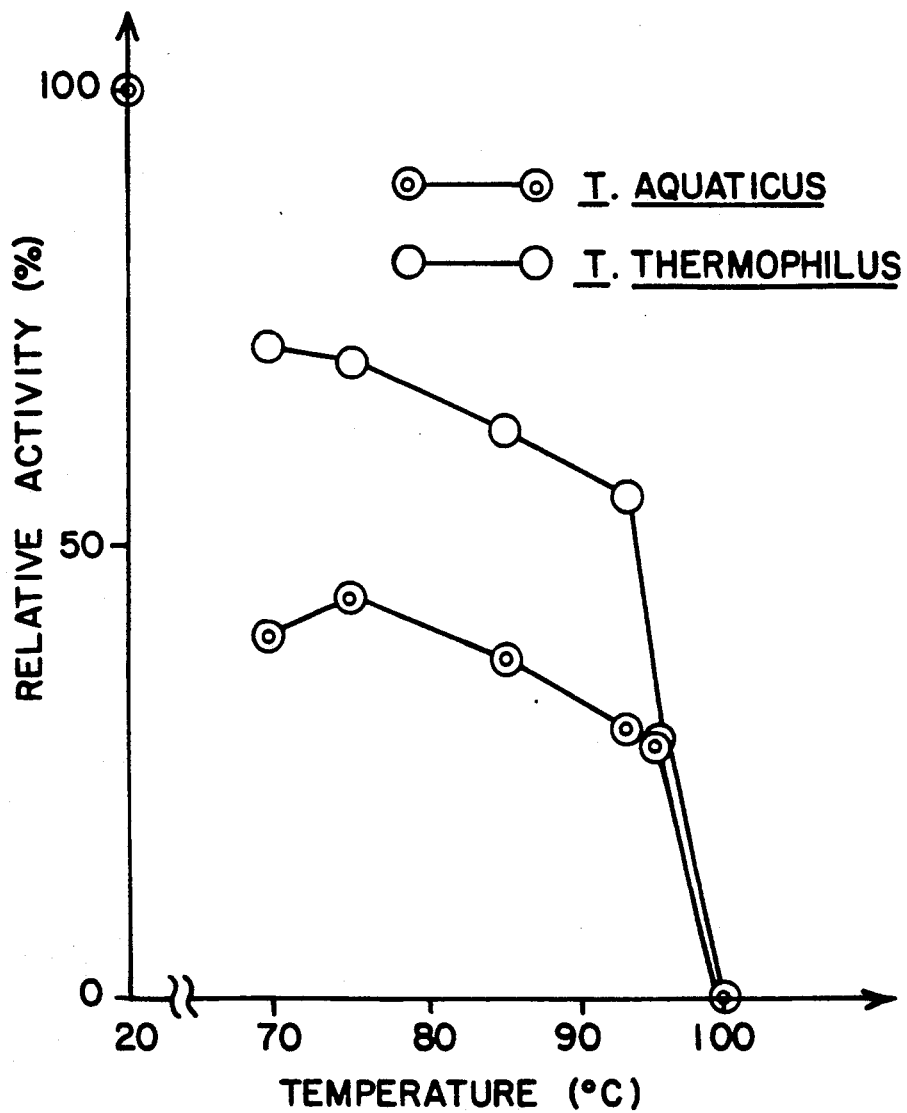
FIG. 5 shows graphs comparing the thermostability of the DNA polymerase of the present invention with that of commercially available Taq polymerase.

The results are also shown in FIG. 5. The single and double circles in this figure indicate values measured using the enzyme of the present invention and the enzyme derived from *Thermus aquaticus* YT-I, respectively.

(6) Molecular weight

The molecular weight of the present enzyme measured by SDS-polyacrylamide gel electrophoresis was approximately 85,000 to 95,000 daltons.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method for producing a DNA polymerase comprising the steps of, culturing a microorganism of the *Thermus thermophilus* in a culture medium, and recovering the produced thermostable DNA polymerase wherein said DNA polymerase has the following characteristics:

(1) it catalyzes the elongation reaction of a nucleotide sequence that is complementary to a template nucleotide sequence, using nucleoside triphosphates as substrates;

(2) its optimal pH is approximately 8.0;

(3) its optimal temperature is approximately 75° C.;

(4) it requires magnesium ions, and the optimal magnesium ion concentration being in the range from 6 to 20 mM;

(5) its optimal saline concentration is approximately 20 to 60 mM of sodium chloride or potassium chloride;

(6) its molecular weight is approximately 85,000 to 95,000 daltons (measured by sodium dodecyl sulfate polyacrylamide gel electrophoresis);

(7) it retains at least about 60% of its activity when placed in a solution comprising 67 mM tris HCL, pH 8.0, 16.6 mM ammonium sulfate, 6.7 mM magnesium chloride, 10 mM 2-mercapoethanol and 170 μg/ml BSA for 2 hours at 85° C.

* * * * *

UNITED STATES PATENT AND TRADEMARK OFFICE
CERTIFICATE OF CORRECTION

PATENT NO. : 5,242,818

DATED : September 7, 1993

INVENTOR(S) : TAIRO OSHIMA, HITOSHI SAKASHITA, HAKUJI MATSUMOTO AND YOSHIHIKO MAEKAWA

It is certified that error appears in the above-identified patent and that said Letters Patent is hereby corrected as shown below:

ON THE TITLE PAGE:

[56] References Cited

OTHER PUBLICATIONS

Second column, lines 4 and 5, delete "Oilgonucleotide" and substitute therefor -- Oligonucleotide --;

Second column, line 7, add "n" to the end of "Ruttiman";

Second column, line 13, delete "Bateriology" and substitute therefor -- Bacteriology --; and Second column, line 16, delete "N" in the word "Nami" and substitute therefor -- n --.

Column 6, Table 1, first column, second line, delete "thermophilus" and substitute therefor -- aquaticus --; and Column 6, Table 1, second column, second line, delete "aquaticus" and substitute therefor -- thermophilus --.

UNITED STATES PATENT AND TRADEMARK OFFICE
CERTIFICATE OF CORRECTION

PATENT NO. : 5,242,818

DATED : September 7, 1993

INVENTOR(S) : Tairo Oshima, Hitoshi Sakashita, Hakuji Matsumoto and Yoshihiko Maekawa It is certified that error appears in the above-identified patent and that said Letters Patent is hereby corrected as shown below:

Column 6, line 35, after "of the" insert "Species".

Signed and Sealed this

Seventeenth Day of May, 1994

Attest:

BRUCE LEHMAN

Attesting Officer

Commissioner of Patents and Trademarks